(12) United States Patent
Sloan (10) Patent No.: US 7,348,883 B2
(45) Date of Patent: Mar. 25, 2008

(54) MEDICAL COMMUNICATION AND LOCATOR SYSTEM AND METHOD

(76) Inventor: Dale A. Sloan, 5520 Abbey Hill Rd., Fort Wayne, IN (US) 46814

( * ) Notice: Subject to any disclaimer, the term of this patent is extended or adjusted under 35 U.S.C. 154(b) by 248 days.

(21) Appl. No.: 11/204,488

(22) Filed: Aug. 16, 2005

(65) Prior Publication Data

US 2006/0033619 A1 Feb. 16, 2006

Related U.S. Application Data

(60) Provisional application No. 60/601,894, filed on Aug. 16, 2004.

(51) Int. Cl.
*G08B 13/14* (2006.01)
(52) U.S. Cl. .................. 340/568.1; 340/286.07
(58) Field of Classification Search ............ 340/568.1, 340/572.1, 825.49, 286.07; 235/375, 376
See application file for complete search history.

(56) References Cited

U.S. PATENT DOCUMENTS

| | | | |
|---|---|---|---|
| 3,668,682 A | 6/1972 | Barbee et al. | |
| 4,225,953 A | 9/1980 | Simon et al. | |
| 4,601,064 A | 7/1986 | Shipley | |
| 4,610,064 A | 9/1986 | Verstraeten | |
| 5,450,070 A | 9/1995 | Massar et al. | |
| 5,455,409 A | 10/1995 | Smith et al. | |
| 5,721,531 A | 2/1998 | Garver et al. | |
| 5,739,765 A | 4/1998 | Stanfield et al. | |
| 5,751,221 A | 5/1998 | Stanfield et al. | |
| 5,760,704 A * | 6/1998 | Barton et al. | 340/825.49 |
| 5,838,223 A | 11/1998 | Gallant et al. | |
| 5,942,986 A * | 8/1999 | Shabot et al. | 340/539.1 |
| 6,133,832 A | 10/2000 | Winder et al. | |
| 6,259,355 B1 | 7/2001 | Chaco et al. | |
| 6,718,341 B1 | 4/2004 | Berstis et al. | |
| 6,825,763 B2 | 11/2004 | Ulrich et al. | |
| 6,861,954 B2 * | 3/2005 | Levin | 340/572.1 |
| 6,870,484 B1 | 3/2005 | Brinsfield et al. | |
| 7,099,895 B2 * | 8/2006 | Dempsey | 340/870.3 |
| 7,154,397 B2 * | 12/2006 | Zerhusen et al. | 340/573.1 |
| 7,158,030 B2 * | 1/2007 | Chung | 340/572.1 |
| 2004/0025780 A1 | 2/2004 | Pharo et al. | |
| 2006/0033619 A1 | 2/2006 | Sloan | |

* cited by examiner

*Primary Examiner*—John Tweel, Jr.
(74) *Attorney, Agent, or Firm*—Frost Brown Todd, LLC (57) ABSTRACT

There is disclosed a medical communication and locator system and method including a medical chart communication system and method and a personnel communication system and method for monitoring the location of charts and personnel in a medical environment. The communication and locator systems may be provided with one-way or two-way communication for locating charts or personnel, contacting needed personnel in the event of an emergency, or for communicating with healthcare workers. A docking station for the communication and locator systems is also disclosed.

20 Claims, 4 Drawing Sheets

MEDICAL COMMUNICATION AND LOCATOR SYSTEM AND METHOD

This application claims the benefit of U.S. Provisional Patent Application entitled "Medical Communication and Locator System And Method", U.S. application Ser. No. 60/601,894 filed on Aug. 16, 2004.

BACKGROUND OF THE INVENTION

In hospitals, and other clinical settings, patient data has traditionally been kept in paper-based medical records. As a patient is cared for, numerous care personnel, including nurses, doctors, and other clinicians, continually update the paper-based medical record with relevant patient information. Containing the relevant care information within a single paper-based medical record generally allows a clinician to quickly ascertain patient condition and the activities of other clinical personnel before making medical decisions. However, the advantages associated with maintaining patient data within a single paper-based file may be minimized if the chart cannot be quickly located or accessed by care personnel.

In fast-paced environments, such as a large, busy emergency room, coronary care unit, intensive care unit, or other hospital unit, charts can be difficult to locate quickly. This is frequently due to the large number of people handling the file, including multiple nurses, laboratory techs, radiology personnel, and physicians. Because the absence of a patient's chart can be debilitating for care personnel, a missing chart is generally accompanied by a frantic "chart search" throughout the hospital floor. A chart search generally involves one or several medical personnel searching from room to room until the chart is found. The time lost in finding a patient's chart may put the patient in jeopardy, may increase the frustration of the staff, and may increase the time and the associated cost of medical procedures. Additionally, for example, in a busy emergency room, time wasted looking for a patient's record may be at the expense of other patients waiting for care.

Although many hospitals have converted paper-based patient files to electronic medical records, paper-based patient files remain the most efficacious means of insuring proper patient care in several clinical areas. For example, in emergency rooms, where numerous medical personnel need to have immediate access to patient data as well as written evaluations of other consultants, the patient records generally stay with the patient as they are evaluated. The value of the paper-based chart in providing immediate access to patient data may be diminished or eliminated entirely if the required data is not readily accessible.

In hospital settings, patients are generally assigned a nurse that looks after their day-to-day needs. In a large, busy, emergency room, as well as other patient care areas, a single nurse may be assigned to care for multiple patients, such that the nurse may not be present when the physician is evaluating the patient. During this evaluation, the nurse is frequently needed to convey information about the patient or to receive orders for patient care. If not present, a "nurse search" generally occurs that includes identifying the assigned nurse and contacting the nurse. To identify the nurse, medical personnel may, for example, contact the emergency room secretary, other nurses, and/or look for the designation on the chart. Once the name is found, personnel generally search for the nurse room to room or try to contact the nurse through an overhead page. Time spent identifying and/or locating the assigned nurse may be substantial, particularly, for example, if the nurse is on break or at lunch. Lost time may put the patient in jeopardy, may increase the frustration of the staff, and may increase the time and the associated cost of medical procedures. Additionally, for example, in a busy emergency room, time wasted looking for a patient's nurse may be at the expense of other patients waiting for care.

Currently, patients generally indicate their desire to be attended to by a nurse or other medical practitioner by signaling a help light, which is often located above their door or at the nurse's station. In a busy clinical environment, such as a large emergency room, a patient's needs may go unattended because the indicators are not seen for extended periods of time. This may be especially true where a single nurse is responsible for a large number of patients.

Even when patient care indicators are responded to quickly by medical personnel, the time required to visit each patient to assess their needs may be substantial. In circumstances where a nurse is responsible for multiple patients, time spent visiting every patient signaling a nurse may detract from the efficiency of the hospital and reduce the time the nurse has to spend with other patients. Time spent addressing minimal patient concerns may reduce the number of patients a nurse can effectively handle or, in the absence of additional nursing staff, may reduce the overall quality of patient care.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

The communication and locator system may comprise a plurality of charts. A "chart" may be any paper and/or electronic collection of patient data, hospital data, and/or patient data associated with a particular patient or a group of patients. Each chart may include a one or more receivers whereby each chart may receive data transmitted by the computer system and/or one or more personnel communicators (discussed below).

Each receiver may include a unique signature to identify each chart individually. The receivers may be any device or combination of devices suitable to receive data transmitted by the computer system and/or one or more personnel communicators, such as an RF receiver, an infrared receiver, an ultrasonic receiver, or the like. Data transmitted and received throughout the system of the present invention may include electronic signals, text or numerical data, voice, images, video, or the like.

Each chart may also include one or more transmitters whereby each chart may transmit data to the computer system and/or one or more personnel communicators (discussed below). Each transmitter may include a unique signature to identify each chart individually. The transmitters may be any device or combination of devices suitable to transmit data to the computer system and/or one or more personnel communicators, such as an RF receiver, an infrared receiver, an ultrasonic receiver, or the like. The receivers and/or transmitters may also be configured such that data may be transmitted and received among the charts.

Each chart may include one or more output devices suitable to communicate information or received data to a user. An output device may include a device, or combination of devices, such as a visual indicator, such as an LED, an LCD screen or the like, an audible indicator such as a speaker, a beeper or the like, or a vibrating electronic motor, or the like. At least one output device may be in communication with one or more chart receivers such that a user or personnel in proximity to a chart may be alerted to data transmitted to the chart.

Each chart may also include one or more input devices to receive input or instructions from a user. An input device may include a device, or combination of devices, such as a quick key, alphanumeric keys or keypad, touch screen, microphone, or the like. At least one input device may be in communication with one or more chart transmitters such that a user may transmit data to the computer system and/or one or more personnel communicators. One or more input devices may be in communication with one or more output devices such that a user may review the inputted data before transmitting the data.

Each chart may include any suitable memory medium for storing patient data and other data, such as a hard drive, magnetic disk, magnetic tape, optical disk, RAM, and the like. Each chart may also include a CPU to, in part, control some of the chart's components and the interactions therebetween. Each chart may also include a power source to power each of the electronic components, such as a rechargeable DC battery pack, solar cells, or the like. Each chart may also include security measures for restricting access to the chart's operation, such as a keycard swipe, personal identification number input device, biometric input device, or the like.

Figure 1:
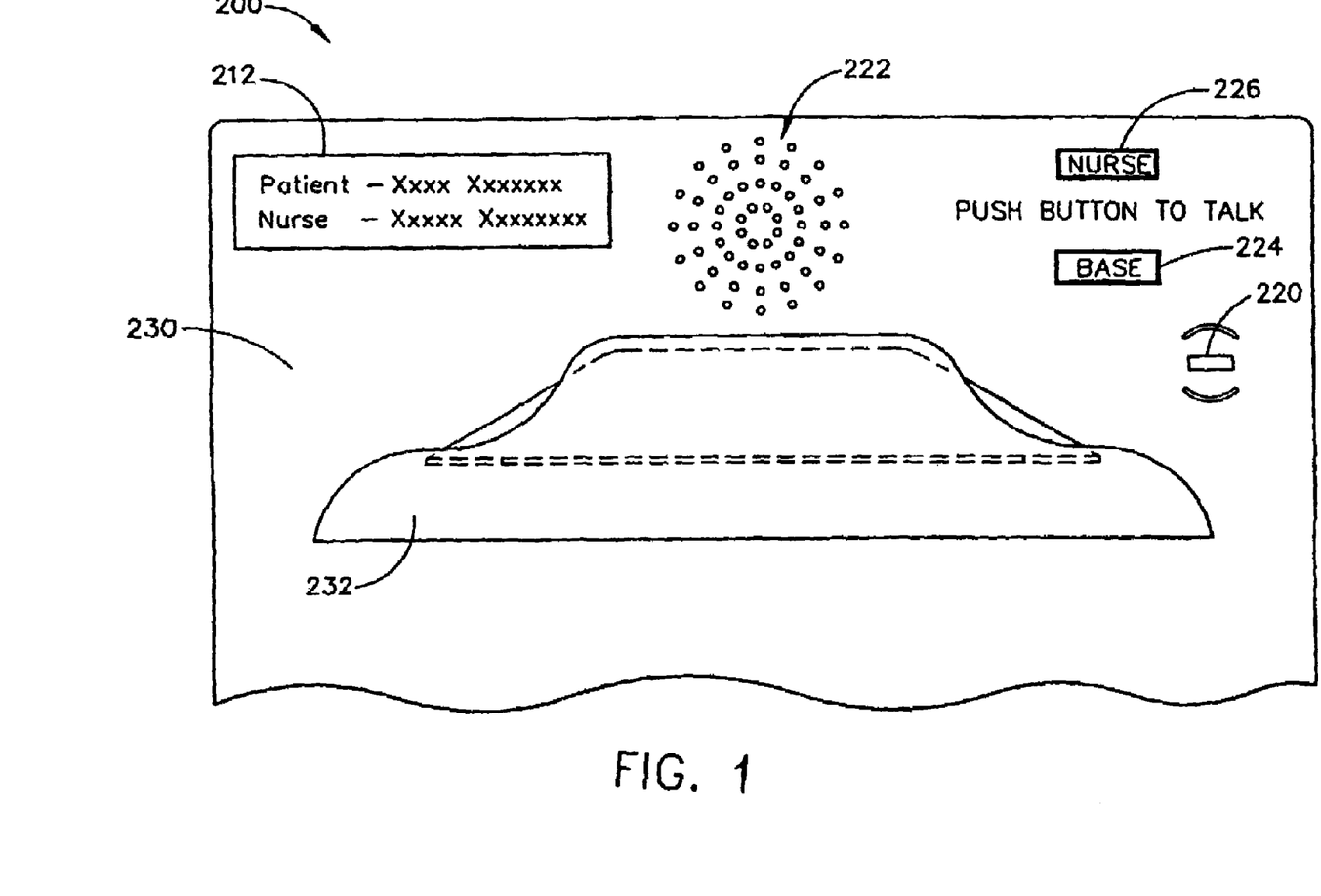
FIG. 1 illustrates a top schematic view of one embodiment of a user interface of a computer system in accordance with the present invention.

FIG. 1 shows an exemplary embodiment of a chart 200 in accordance with the present invention. Chart 200 includes a support 230 and a clip 232. The output devices, a visual display 212 and a speaker 222, may be coupled to the support 230 via mechanical fasteners, adhesive, ultrasonic welding or the like. The input devices, quick keys 224, 226 and microphone 220, may be coupled to the support 230 via mechanical fasteners, adhesive, ultrasonic welding or the like. Transmitter (not shown) and receiver (not shown), may be enclosed within the support 230, or an enclosure secured to the support 230, to protect them from dust, fluid, and the like.

Visual display 212 may display patient's name, nurse's name or other useful information and may be in communication with the chart's receiver. Visual display 212 may be a device such as an LCD screen, or may include one or more LEDs, such that the visual display 12 may alert a user, or personnel in proximity to the chart, that data has been transmitted to the chart. For example, if the LEDs of a visual display 212 of a chart are activated, it may indicate to a user, or personnel in proximity to the chart, that the chart is needed by other personnel.

Speaker 222 may also alert a user, or personnel in proximity to the chart, that data has been transmitted to the chart and may be in communication with the chart's receiver. For example, if the speaker 222 of a chart emits a certain tone or sound, it may indicate to a user, or personnel in proximity to the chart, that the chart is needed by other personnel. Alternatively, speaker 222 may serve to facilitate verbal communication between a user of the computer system or a personnel communicator of a nurse or nurses associated with the chart and/or chart's patient(s).

Quick keys 224, 226, in communication with the chart's transmitter, may be configured to facilitate communication between the computer system or a personnel communicator of a nurse or nurses associated with the chart and/or chart's patient(s). For example, a user may engage the "NURSE" quick key 226 and speak into the microphone 220 to verbally communicate with the nurse associated with the chart 200 via the nurse's personnel communicator. Alternatively, pressing the "NURSE" quick key 226 may simply alert the nurse, via the nurse's personnel communicator, that the chart or chart's patient(s) need the nurse's attention. The "BASE" quick key 224 may facilitate similar communication between the computer system and the chart.

The communication and locator system may also comprise a plurality of personnel communicators. In one embodiment, nurses, physicians, technologists, administrators, ambulance personnel, and/or emergency medical personnel may be provided with communicators. Each communicator may include one or more receivers whereby each communicator may receive data transmitted by the computer system and/or one or more charts. Each receiver may include a unique signature to identify each communicator individually. The receivers may be any device or combination of devices suitable to receive data transmitted by the computer system and/or charts, such as an RF receiver, an infrared receiver, an ultrasonic receiver, or the like.

Each communicator may also include one or more transmitters whereby each communicator may transmit data to the computer system and/or one or more charts. Each transmitter may include a unique signature to identify each communicator individually. The transmitters may be any device or combination of devices suitable to transmit data to the computer system and/or the charts, such as an RF receiver, an infrared receiver, an ultrasonic receiver, or the like. The receivers and/or transmitters may also be configured such that data may be transmitted and received among the communicators. The personnel communicators may also be adapted to communicate with other pagers, cell phones, an overhead intercom system, or the like.

Each communicator may include one or more output devices suitable to communicate information or received data to a user. An output device may include a device, or combination of devices, such as a visual indicator, such as an LED, an LCD screen or the like, an audible indicator such as a speaker, a beeper or the like, or a vibrating electronic motor, or the like. At least one output device may be in communication with one or more communicator receivers such that a user may be alerted to data transmitted to the communicator. One or more output devices may be configured to generate a plurality of specific outputs whereby each specific output has a specific meaning relating to source of the transmission, where personnel attention is needed, urgency of communication, or the like. It will be readily apparent to those of ordinary skill in the art that multiple variations and configurations of output devices comprising visual indicators, audible indicators, vibrating indicators, and combinations thereof, are within the scope of the present invention.

Each communicator may also include one or more input devices to receive input or instructions from a user. An input device may include a device, or combination of devices, such as a button, alphanumeric keys or keypad, touch screen, microphone, or the like. At least one input device may be in communication with one or more transmitters such that a user may transmit data to the computer system and/or one or more charts. One or more input devices may be in communication with one or more output devices such that a user may review the inputted data before transmitting the data.

Illustratively, a personnel communicator may, for example, be a pager, a cell phone, a walkie-talkie, a two-way communicator, a BLACKBERRY, a personal digital assistant (PDA), a flashing indicator, a vibrating indicator, an audible indicator, or any other device suitable for receiving and/or transmitting data to and from personnel. In one embodiment, nurses or other medical personnel, may each be provided with personnel communicators having unique frequency signatures associated with the individual's name, position, or other suitable designator.

The personnel communicators may be carried or worn, such as on a belt, waistband, or wrist, and may be provided with suitable features to facilitate communication such as, for example, headsets or ear pieces. The personnel communicators may be rechargeable, may require the replacement of batteries, and/or may otherwise be powered by any suitable power source.

Alternatively, patients may also be provided with communicators, where patients may send and receive information and/or requests from medical personnel, administrative personnel, and/or other suitable individuals. Communicators for patients may, for example, include only a basic call button or may be a more complex communication unit. In a further embodiment, patients may be given communicators with greater functionality, where features of communicator, such as two-way communication, may be accessible or inaccessible depending upon the status of the patient.

Figure 2:
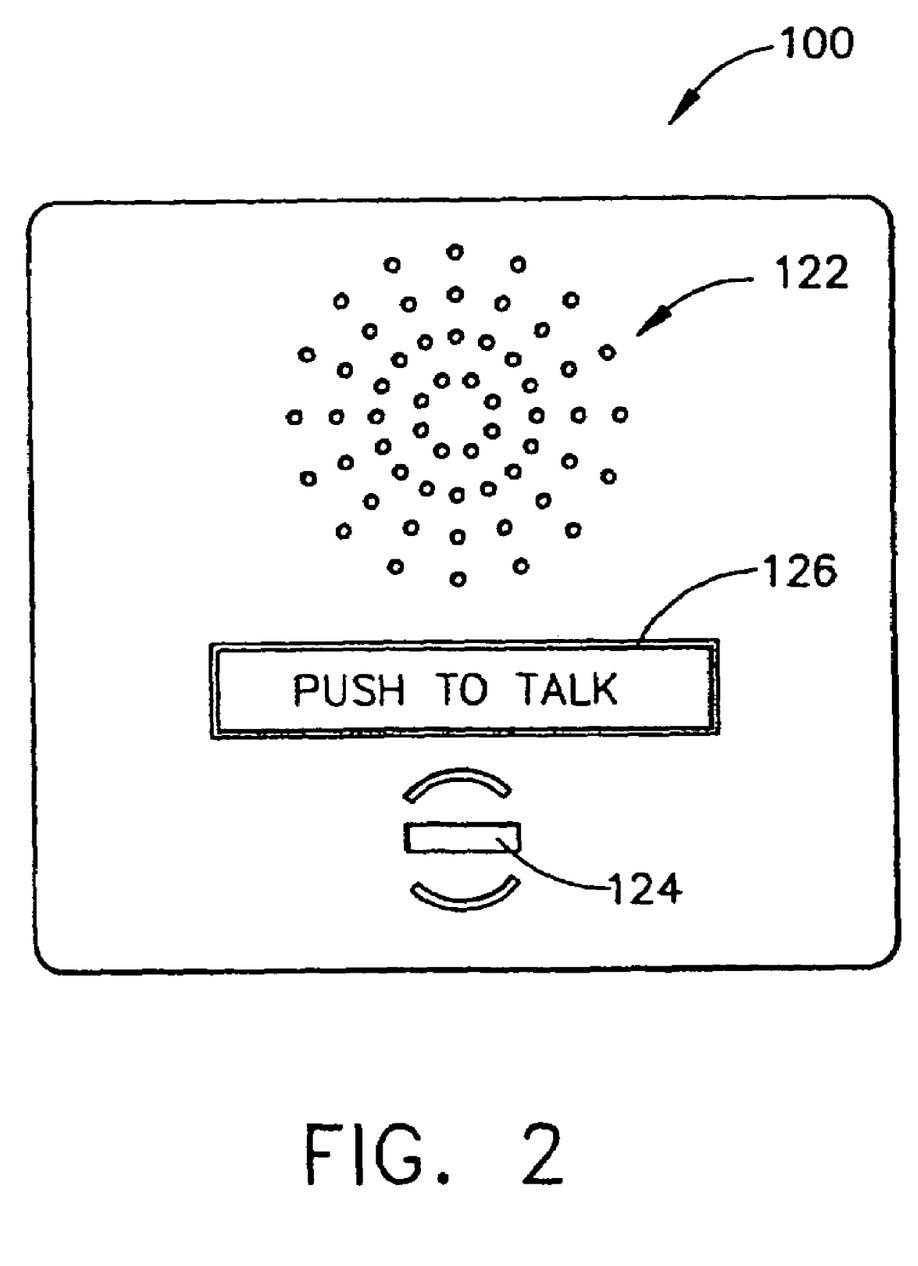
FIG. 2 illustrates a front schematic view of one embodiment of a personnel communicator in accordance with the present invention.

FIG. 2 shows an exemplary embodiment of a personnel communicator 100 in accordance with the present invention. Personnel communicator may comprise a body. A speaker 122 and a microphone 124 may be protectively enclosed within the body. Transmitter (not shown) and receiver (not shown), may also be enclosed within the body to protect them from dust, fluid, and the like. Personnel communicator may also include a communication button 126 integral with the body.

Speaker 122, in communication with the communicator's receiver, may alert a user that data has been transmitted to the communicator 100. Speaker 122 may also serve to facilitate verbal communication between a user of the computer system or a user of a chart. Alternatively, speaker 122 may be configured to emit multiple specific tones or sounds, where each specific tone or sound has a specific meaning relating to source of the transmission, where personnel attention is needed, urgency of communication, or the like. Similarly, if the communicator included a visual indicator capable of emitting different colored light, such as LEDs and the like, the visual indicator may be configured such that each color has a specific meaning relating to source of the transmission, where personnel attention is needed, urgency of communication, or the like.

Communication button 126, in communication with the communicator's transmitter, may be configured to facilitate communication between the user of a communicator and the computer system or a chart. For example, a user may engage the communication button 126 and speak into the microphone 124 to verbally communicate with a user of the computer system or of a chart.

The communication and locator system may also comprise a computer system configured to receive, store and retrieve patient data. Patient data may be any clinical or administrative information related to a patient's care or condition including, but not limited to, patient name, patient's room, nurse(s) assigned to particular patients, code information, back-up nursing information, electronic medical charts, billing information, insurance information, medical histories, nursing histories, primary physicians, drug allergies, patient requests, etc. The computer system may include a user interface suitable to communicate information to a user as well as receive input or instructions from a user. The user interface may include one or more devices such as a monitor, speaker(s), keyboard, alphanumeric keypad, touch screen, mouse, microphone, voice activated device, lights, or the like.

The computer system may include any suitable memory medium for storing patient data and other data, such as a hard drive, magnetic disk, magnetic tape, optical disk, RAM, and the like. The computer system may also include a processor adapted to retrieve and display data for a user based on a user's input. Illustratively, the computer system may be a laptop PC, a desktop PC or the like. In one embodiment, the computer system may be powered by an AC outlet, a portable power source, such as a DC battery, or both. In one embodiment, where the computer system is powered by a portable DC power supply, the computer system may be provided with wheels such that the device may be moved to a suitable location depending on the clinical needs.

The computer system may include a network, such as the internet or an intranet, wherein patient data and the like may be stored remotely and where users access the data via the network at one or more workstations located within the clinical environment or via a home PC, or the like. Each workstation may be a laptop PC, a desktop PC, a terminal, or the like. The workstations may be in communication with the network via an Ethernet connection, a wireless connection, or the like. The workstations may be located throughout the clinical environment such that medical personnel may have convenient access to the system. For example, one or more workstations may be located at an entrance to an emergency room, at the nurses' station, etc. In one embodiment, the workstations may be powered by an AC outlet, a portable power source, such as a DC battery, or both. In one embodiment, where the workstations are powered by a portable DC power supply, the workstations may be provided with wheels such that the workstations may be moved to a suitable location depending on the clinical needs. In a further embodiment of the present invention, multiple workstations may be positioned throughout a hospital floor, where some workstations may be fixed and others portable.

The computer system may also include one or more transmitters and/or one or more receivers for providing communication between the computer system and the charts and/or the personnel communicators. The transmitters and/or receivers may be in communication with the user interface. The transmitters and/or receivers may be any device or devices suitable for providing communication between the computer system and the charts and/or the personnel communicators, such as, an RF transmitter and/or receiver, an infrared transmitter and/or receiver, an ultrasonic transmitter and/or receiver, a combination thereof, or the like. The computer system may be configured to transmit data to each personnel communicator or chart based on the communicator's or chart's unique address. Also, computer system may be configured to identify the source of received data based on the unique signature associated with the transmitter of a personnel communicator or chart. Computer system may facilitate communication between the personnel communicators and/or the charts; for example, data transmitted by a personnel communicator or chart may first be received by the computer system and then re-transmitted to the appropriate personnel communicator or chart. Alternatively, communication between the personnel communicators and/or the charts may be direct and not necessarily always involve the computer system. The computer system may also have access to an overhead intercom system.

The computer system may also include security measures for restricting access thereto, such as a keycard swipe, personal identification number input device, biometric input device, or the like. Computer system may store the names of acceptable users and their corresponding access codes, where access to patient data, medical data, and/or administrative data may be denied unless a correct entry is submitted. A further embodiment of the present invention includes providing access to different levels of information depending on the user's level of authorization. For example, a physician may be provided with a keycard giving them access to all of the information in the system, whereas a laboratory tech may be restricted to only those files on which they are directly involved.

The computer system may also be provided with alarm indicators which may, for example, be lights and/or audible alarms that may be triggered when medical personnel signal, for example, a code blue. The alarm indicators may be triggered from personnel communicators, charts, a workstation, an internal hospital network, or by any other suitable means. In addition, the computer system may include a database wherein the identification of a predetermined individual or personnel are associated with certain medical conditions such that the computer system may transmit data to the predetermined individuals or personnel upon an input from a user or a personnel communicator. For example, if a code blue is input or received from a personnel communicator, the computer system may transmit the code blue to a predetermined doctor, respiratory therapists, nurses, or the like.

Figure 3:
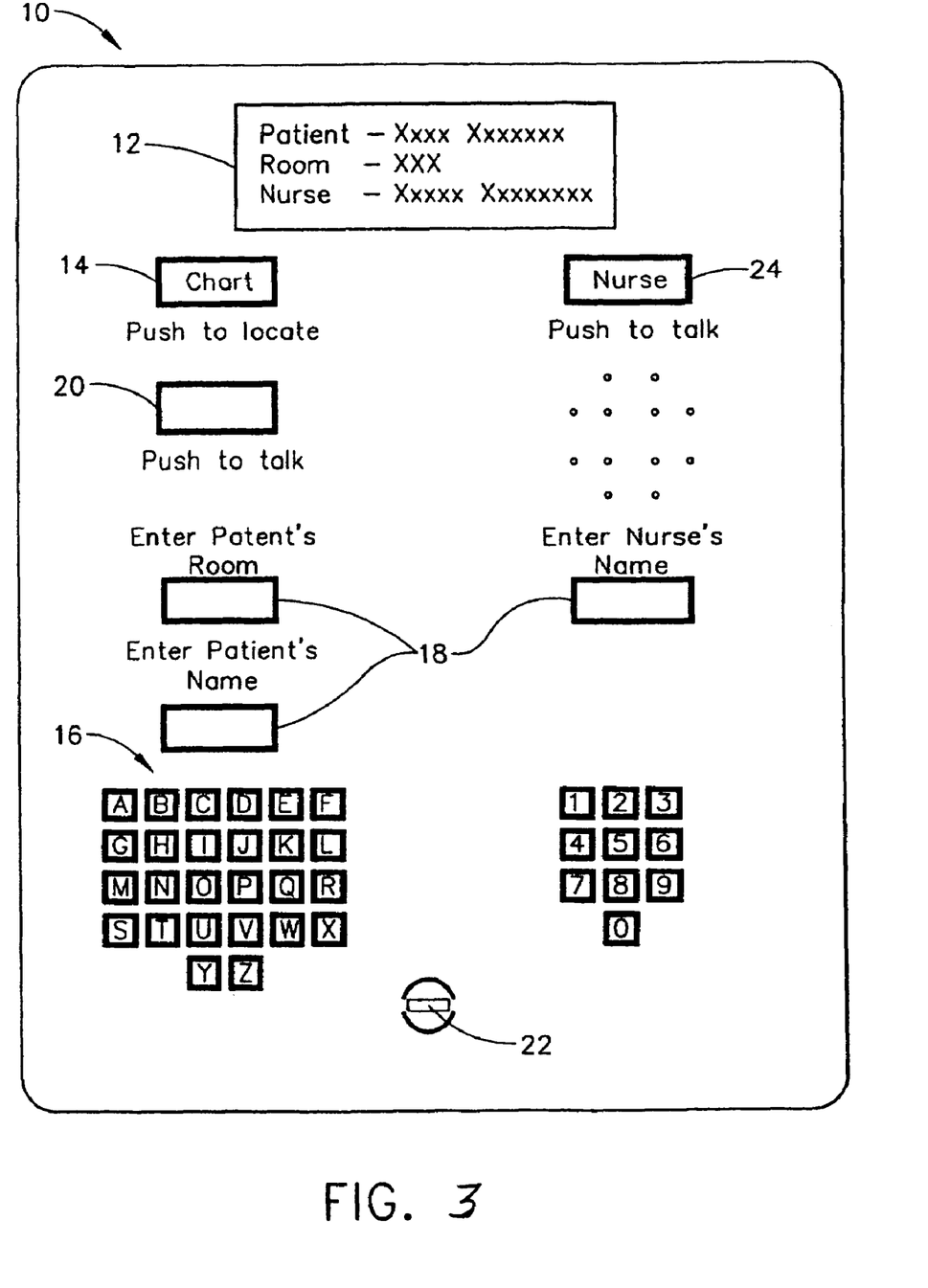
FIG. 3 illustrates a partial top schematic view of one embodiment of a chart in accordance with the present invention.

FIG. 3 shows an exemplary embodiment of a user interface 10 of the computer system in accordance with the present invention. A visual display 12, such as an LCD screen, may display patient data, such as Patent, Room, Nurse, and other data. User interface 10 may include an alphanumeric keypad 16 whereby a user may input data.

User interface 10 may also include one or more shortcuts 18 to prompt user and/or the computer system for specific information. The shortcuts 18 may include, "ENTER NURSE'S NAME", "ENTER PATIENT ROOM", "ENTER PATIENT NAME" or any other desirable prompts or configurations. For example, if a user knows the name of a patient, but not their room number or primary nurse, the user may press the "ENTER PATIENT NAME" shortcut and may be prompted by visual display 12 to input the patient's name via keypad 16. Once the patient's name has been entered, the computer system may be programmed to retrieve and display data associated with the patient name such as, for example, the primary nurse or room number.

User interface may also include a chart locator quick key 14. Engaging the chart locator quick key 14 may result in a prompt on visual display 12 querying the user as to which chart is desired. In one embodiment, the user may then input a chart identifier, such as a patient number, a patient name, a nurse's name, a room number, chart number, or other suitable information. In response to the inputted information, visual display 12 may list one or more charts by chart identifiers associated with the user's input. The user may then select the desired chart from the list. Upon selection of a chart from the list, computer system will transmit a location signal to the desired chart's unique address. Visual display 12 may inform user that the location signal has been sent.

User interface may also include a chart communication quick key 20. Engaging the chart communication quick key 20 may result in a prompt on visual display 12 querying the user as to which chart they wish to communicate with. In one embodiment, the user may then input a chart identifier, such as a patient number, a patient name, a nurse's name, a room number, chart number, or other suitable information. In response to the inputted information, visual display 12 may list one or more charts by chart identifiers associated with the user's input. The user may then select the desired chart from the list. Upon selection of a chart from the list, the user may speak into the microphone 22, or input communication via the keypad 16, and computer system will transmit the communication to the desired chart's unique address. Visual display 12 may inform the user that the communication has been sent.

User interface may also include a personnel communicator quick key 24. Engaging the chart communication quick key 24 may result in a prompt on visual display 12 querying the user as to which personnel they wish to communicate with. Personnel may be identified specifically by name, position, group, association with a patient, by room number, or by any other suitable indicator. The user may then input a personnel identifier. In response to the inputted information, visual display 12 may list personnel associated with the user's input. The user may then select the desired person or personnel from the list. Upon selection, the user may speak into the microphone 22, or input communication via the keypad 16, and computer system will transmit the communication to the personnel communicator's unique address. Visual display 12 may inform user that the communication has been sent.

The user interface 10 may also include a speaker which may alert a user that data has been transmitted to the computer system by a chart and/or personnel communicator. Speaker may serve to facilitate verbal communication between a user of the computer system and a user of a chart and/or personnel communicator. Alternatively, the speaker may be configured to emit multiple specific tones or sounds, where each specific tone or sound has a specific meaning relating to source of the transmission, where personnel attention is needed, urgency of communication, or the like.

Figure 4:
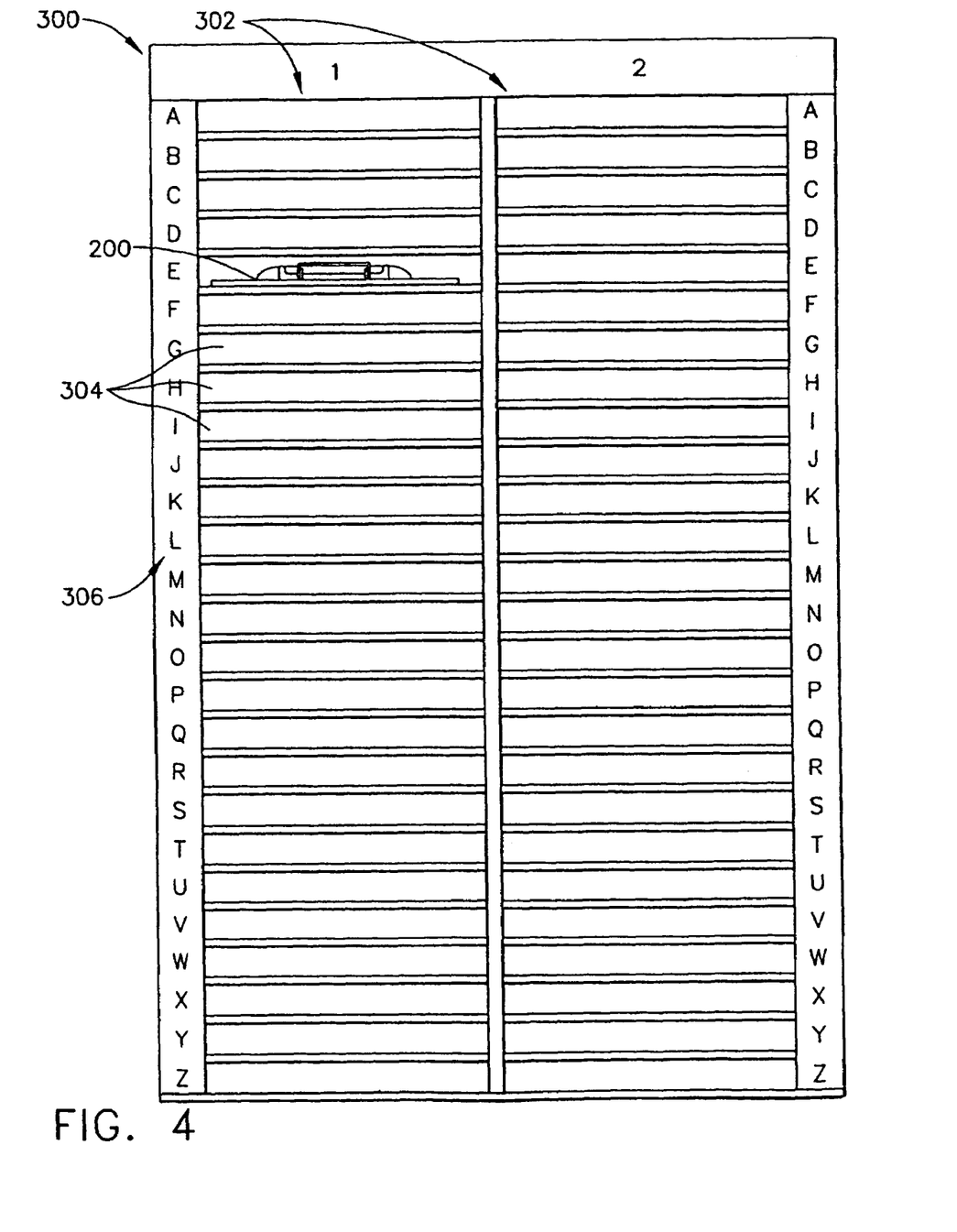
FIG. 4 illustrates a front schematic view of one embodiment of a chart rack for the chart of FIG. 3.

Referring now to FIG. 4, the communication and locator system may also comprise a chart rack 300 adapted to charge charts 200. Chart rack 300 may be provided with one or a plurality of columns 302 having one or a plurality of docks 304. Each dock 304 may be given its own designator as shown on key 306, such as a letter of the alphabet or room number, where a patient's chart may be stored in a dock 304 associated with their name. In one embodiment, chart 200, having electronic functionality, may be provided with an AC adapter and/or coupling, which may be plugged into a corresponding coupling on chart rack 300 to recharge the DC power source of chart 200. In the rechargeable embodiment of chart 200, chart 200 may be recharged by an AC coupling through chart rack 300 or by any other suitable means known in the art. In a further embodiment of the present invention, power may be restored to chart 200 by replacing batteries, charging solar cells, plugging chart 200 into an AC wall outlet, or by any other suitable means.

Chart rack 300 may be positioned, for example, near the computer system, or workstation thereof, to provide users with easy access to charts 200 when they are reviewing medical and/or patient data. When charts 200 are returned to chart rack 300 they may be recharged, such that charts 200 are continuously charging when not in use. In a further embodiment of the present invention, charts 200 may be docked in chart racks located within patient rooms or coupled with a patient's bed. For example, chart rack 300 may serve as a chart 200 storage rack when charts 200 are not in use, where charts 200 may be transferred to a docking station (not shown) on a patient's bed or in a patient's room when retaining the file in close proximity to the patient at all times is desirable. Patient and/or room docking stations may also be adapted to recharge a DC battery unit of chart 200. In another embodiment of the present invention, charts 200 placed in chart rack 300 or other suitable chart racks, such as within a patient's room, may be adapted to communicate with the computer system, where a user accessing chart 200 through the computer system may be informed of the chart's 200 location. Chart rack 300 may, in one embodiment, include a display (not shown), where the display may be any suitable display, such as a computer monitor, indicating which charts are present and the location of the charts in the chart rack. An alternative embodiment of chart rack 300 includes providing multiple displays, such as LCD displays, next to each dock 304, where the display may indicate specific patient information for that dock. In a further embodiment, charts 200 may be provided with displays that are visible when the charts 200 are inserted into chart rack 300 where, for example, physicians may view basic patient information without removing chart 200 from chart rack 300.

The foregoing is considered as illustrative only of the principles of the invention. For example, the communication and location device of the present invention may be applied to other fields, such as the legal field, manufacturing field, warehousing, etc., where locating charts or other objects and/or locating and communicating with multiple personnel is desirable. Further, since numerous changes and modifications will readily occur to those skilled in the art, it is not desired to limit the invention to the exact construction and operation shown and described, and accordingly, all such suitable changes or modifications in structure or operation which may be resorted to are intended to fall within the scope of the claimed invention.

The invention claimed is:

1. A communication system, comprising:
   a. a plurality of charts, each chart comprising:
      i. a support;
      ii. a chart receiver coupled to said support, said chart receiver comprising a unique electronic chart address, and said chart receiver being operable to receive transmitted data corresponding to said unique chart address;
      iii. a chart output device coupled to said support and in communication with said chart receiver, said chart output device being operable to produce an output upon said chart receiver's receipt of said transmitted data;
   b. a plurality of personnel communicators, each communicator comprising:
      i. a body;
      ii. a communicator receiver coupled to said body, said communicator receiver comprising a unique electronic communicator address, and said communicator receiver being operable to receive transmitted data corresponding to said unique communicator address;
      ii. a communicator output device coupled to said body and in communication with the communicator receiver, said communicator output device being operable to produce an output upon said communicator receiver's receipt of said transmitted data; and
   c. a computer system configured to receive and retrieve data, comprising:
      i. a chart communication transmitter operable to transmit data corresponding to at least one unique chart address of at least one of said plurality of charts; and operable to transmit data corresponding to at least one unique chart address of at least one of said plurality of charts.

2. A communication system, comprising:
   a. at least one chart, each of said at least one chart comprising:
      i. a support,
      ii. a chart receiver associated with said support, said chart receiver comprising a unique chart address, where said chart receiver is operably configured to receive patient data corresponding to said unique chart address, and
      iii. a chart output device associated with said support and said chart receiver, where said chart output device is operably configured to selectively produce an output in response to the receipt of patient data by said chart receiver; and
   b. a computer system, comprising:
      i. an output device,
      ii. an interface operably configured to receive patient data and to communicate patient data to a user via said output device,
      iii. a memory medium for storing patient data, and
      iv. a chart communication transmitter operably configured to transmit patient data.

3. The communication system of claim 2, wherein said at least one chart further comprises a chart transmitter associated with said support, where said chart transmitter is operably configured to transmit patient data.

4. The communication system of claim 3, wherein said chart transmitter and said chart receiver are operably configured to respectively send and receive patient data from devices selected from the group consisting of said at least one chart, a pager, a communicator, a cell phone, said computer system, a dock, an intercom system, and combinations thereof.

5. The communication system of claim 2, wherein said computer system comprises a chart communication receiver operably configured to receive patient data.

6. The communication system of claim 2, further comprising at least one communicator, each of said at least one communicator comprising:
   i. a body,
   ii. a communicator receiver associated with said body, said communicator receiver comprising a unique electronic communicator address, where said communicator receiver is operably configured to receive patient data corresponding to said unique communicator address, and
   iii. a communicator output device associated with said body and configured to communicate with said communicator receiver, where said communicator output device is operably configured to produce an output upon the receipt of patient data by said communicator receiver.

7. The communication system of claim 6, wherein said at least one communicator is organized into at least one group configured to communicate with said computer system, where patient data may be transmitted to said at least one group via said interface such that said at least one communicator does not have to be accessed individually.

8. The communication system of claim 6, wherein said at least one communicator and said interface are operably configured for two-way verbal communication therebetween.

9. The communication system of claim 6, further comprising a communication transmitter associated with said body configured to communicate with a communicator input accessible by a user, where patient data may be transmitted from each of said at least one communicator via said communication transmitter.

10. The communication system of claim 2, wherein said chart communication transmitter is operably configured to send patient data to devices selected from the group consisting of said at least one chart, a pager, a communicator, a cell phone, said computer system, a dock, an intercom system, and combinations thereof.

11. The communication system of claim 10, wherein said chart communication transmitter is operably configured to send patient data to each of said at least one chart.

12. The communication system of claim 2, wherein patient data is information selected from the group consisting of clinical information, administrative information, patient name, patient room number, the patient assigned nurse, code information, back-up nursing information, electronic medical charts, billing information, insurance information, medical histories, nursing histories, primary physicians, drug allergies, patient requests, and combinations thereof.

13. The communication system of claim 2, wherein said chart output device is a device selected from the group consisting of a visual output device, an audio output device, a textual output device, a video output device, at least one light, an alarm, an LED screen, a speaker, and combinations thereof.

14. The communication system of claim 2, wherein a plurality of said at least one chart are organized into at least one group associated with said computer system.

15. The communication system of claim 2, wherein said at least one chart and said interface are operably configured for two-way verbal communication therebetween.

16. The communication system of claim 2, wherein said at least one chart comprises a memory medium for storing patient data.

17. A docking system, comprising:
   a. at least one chart, each of said at least one chart comprising:
      i. a support,
      ii. a chart receiver associated with said support, said chart receiver comprising a unique chart address, where said chart receiver is operably configured to receive transmitted patient data corresponding to said unique chart address,
      iii. a chart output device associated with said support and configured to communicate with said chart receiver, where said chart output device is operably configured to produce an output upon said chart receiver's receipt of patient data, and
      iv. a chart transmitter associated with said support, where said chart transmitter is operably configured to transmit patient data; and
   b. a docking station, said docking station comprising:
      i. at least one dock,
      ii. a docking transmitter, where said docking transmitter is associated with said docking station,
      iii. a docking receiver, where said docking receiver is associated with said docking station and is operably configured to receive patient data transmitted from said at least one chart, and
      iv. a docking output, where said docking output is coupled with said docking station and is operably configured to display patient data received via from said docking receiver.

18. The docking system of claim 17, wherein said docking station includes a power supply operably configured to recharge said at least one chart.

19. The docking system of claim 17, wherein said docking transmitter and said docking receiver are operably configured to communicate with a device selected from the group consisting of said at least one chart, a pager, a communicator, a cell phone, said computer system, a dock, an intercom system, and combinations thereof.

20. The docking system of claim 19, wherein said docking station is operably configured to transmit data to said at least one computer system indicating which of said at least one chart is stationed at said docking station.

* * * * *